(12) United States Patent
Klurfeld et al.

(10) Patent No.: US 10,835,693 B2
(45) Date of Patent: Nov. 17, 2020

(54) COMPACT MODULAR INHALER, VAPORIZER FOR WEARABLE MULTIFUNCTIONAL WATCH

(71) Applicants: Peter Daniel Klurfeld, Encino, CA (US); Douglas Cohen, Venice, CA (US); Elliott Galynsky, Van Nuys, CA (US)

(72) Inventors: Peter Daniel Klurfeld, Encino, CA (US); Douglas Cohen, Venice, CA (US); Elliott Galynsky, Van Nuys, CA (US)

( * ) Notice: Subject to any disclaimer, the term of this patent is extended or adjusted under 35 U.S.C. 154(b) by 0 days.

(21) Appl. No.: 16/232,869

(22) Filed: Dec. 26, 2018

(65) Prior Publication Data
US 2020/0206439 A1 Jul. 2, 2020

Related U.S. Application Data

(63) Continuation-in-part of application No. 15/264,508, filed on Sep. 13, 2016.

(51) Int. Cl.
*A61M 11/04* (2006.01)
*G04B 47/00* (2006.01)
(Continued)

(52) U.S. Cl.
CPC ........... *A61M 11/042* (2014.02); *A24F 47/00* (2013.01); *A24F 47/008* (2013.01); *A61M 11/00* (2013.01);
(Continued)

(58) Field of Classification Search
CPC .... A61M 11/00; A61M 11/04; A61M 11/041; A61M 11/042; A61M 11/044;
(Continued)

(56) References Cited

U.S. PATENT DOCUMENTS 6,223,744 B1 * 5/2001 Garon .................. A61M 15/00
128/200.14
2015/0264978 A1 9/2015 Arnel
(Continued)

FOREIGN PATENT DOCUMENTS

CN 104872823 9/2015

OTHER PUBLICATIONS

PCT International Search Report and Opinion (Clean).

*Primary Examiner* — Colin W Stuart
(74) *Attorney, Agent, or Firm* — William J. Benman; Benman, Brown & Williams

(57) ABSTRACT

A compact wearable modular multifunctional inhalation device of the present invention. In the illustrative embodiment, the device includes a housing with at least one port; a removable cartridge module adapted to seat within the housing, the cartridge including: a source of inhalant mounted within the cartridge for providing inhalant into the port and a heating element mounted within the cartridge for heating the inhalant; a removable modular electronic circuit adapted to seat within the housing to provide electrical current to the heating element; and a mechanism coupled to the housing for wearing the device. The electronic circuit may include a processor and memory. A removable modular electronic display is adapted to seat within the housing and connect electrically with the circuit. Software is stored in the memory for execution by the processor for activating the heating element. The software includes code for monitoring the status of the inhalant and/or the source of electrical potential. A switch, activated by air flow, is included for activating the heating element.

17 Claims, 15 Drawing Sheets

(51) Int. Cl.
*A24F 47/00* (2020.01)
*A61M 11/00* (2006.01)

(52) U.S. Cl.
CPC ........... *A61M 11/04* (2013.01); *A61M 11/041* (2013.01); *G04B 47/00* (2013.01); *A61M 2205/33* (2013.01); *A61M 2205/3334* (2013.01); *A61M 2205/3584* (2013.01); *A61M 2205/50* (2013.01); *A61M 2205/52* (2013.01); *A61M 2205/583* (2013.01); *A61M 2205/587* (2013.01); *A61M 2205/8206* (2013.01); *A61M 2209/088* (2013.01)

(58) Field of Classification Search
CPC ............... A61M 15/00; A61M 15/0001; A61M 15/0021; A61M 15/0065; A61M 15/0068; A61M 15/0071; A61M 15/008; A61M 15/0091; A61M 15/0095; A61M 15/06; A61M 2205/33; A61M 2205/3334; A61M 2205/3584; A61M 2205/50; A61M 2205/583; A61M 2205/587; A61M 2205/8206; A61M 2209/008; A61M 2209/088; A24F 47/00; A24F 47/002; A24F 47/004; A24F 47/008; G04B 47/00; G04B 47/006; G04B 47/04; G04B 47/046; G04B 47/06; A62B 7/00; A62B 9/00

See application file for complete search history.

(56) References Cited

U.S. PATENT DOCUMENTS

| | | | |
|---|---|---|---|
| 2015/0282527 A1* | 10/2015 | Henry, Jr. ............. | A24F 47/008 131/328 |
| 2016/0029697 A1* | 2/2016 | Shafer ................... | A24F 47/008 131/328 |
| 2016/0082208 A1* | 3/2016 | Ballam ............. | A61M 16/0003 128/200.14 |
| 2016/0101248 A1* | 4/2016 | Baldwin ........... | A61M 15/0021 128/200.14 |
| 2016/0174607 A1* | 6/2016 | Montgomery ........ | A24F 47/004 128/202.21 |
| 2017/0106152 A1 | 4/2017 | Klurfeld | |
| 2018/0132530 A1 | 5/2018 | Rogers et al. | |

\* cited by examiner

COMPACT MODULAR INHALER, VAPORIZER FOR WEARABLE MULTIFUNCTIONAL WATCH

REFERENCE TO RELATED APPLICATION

This is a Continuation-in-Part of U.S. patent application Ser. No. 15/264,508 filed Sep. 13, 2016 by P. D. Klurfeld, the teachings of which are incorporated herein by reference.

BACKGROUND OF THE INVENTION

Field of the Invention

The present invention relates to health-related devices. More specifically, this invention relates to inhalers and vaporizers.

Description of the Related Art

An inhaler is a device used for delivering medication via inhalation. Inhalers typically use a compressed-gas propellant to deliver a metered dose of medicine. When the inhaler is activated, a fixed amount of the medicine is suspended in the propellant and is expelled from the mouthpiece of the inhaler. Vaporizers are devices used to turn active ingredients of plant material and/or other herbs or blends, chemical mixtures i.e. salt solutions or other synthetic compounds to vapor for the purpose of inhalation. An atomizer is a device, typically electrically connected to a heating element, for emitting water, perfume, or other liquids as a fine spray or vapor.

A need existed in the art for a compact inhaler, vaporizer or atomizer A compact implementation of an inhaler, vaporizer or atomizer would allow for the device to be worn on the body thereby making it available to a patient or user for medical emergencies or simple convenience.

The need in the art was addressed by U.S. patent application Ser. No. 15/264,508 entitled Wearable Multifunctional Inhaler, Vaporizer Watch filed Sep. 13, 2016 by P. D Klurfeld, the teachings of which are incorporated herein by reference. This application disclosed and claimed a novel wearable multifunctional inhaler and vaporizer incorporated into a watch.

However, a need remains in the art for a more compact, versatile and cost effective multifunctional inhaler vaporizer design and construction.

SUMMARY OF THE INVENTION

The need in the art is addressed by the compact wearable modular multifunctional inhalation device of the present invention. In the illustrative embodiment, the device includes a housing with at least one port; a removable cartridge module adapted to seat within the housing, the cartridge including: a source of inhalant mounted within the cartridge for providing inhalant into the port and a heating element mounted within the cartridge for heating the inhalant; a removable modular electronic circuit adapted to seat within the housing to provide electrical current to the heating element; and a mechanism coupled to the housing for wearing the device.

The electronic circuit may include a processor and memory. A removable modular electronic display is adapted to seat within the housing and connect electrically with the circuit. Software is stored in the memory for execution by the processor for activating the heating element. The software includes code for monitoring the status of the inhalant and/or the source of electrical potential. A switch, activated by air flow, is included for activating the heating element. The software also includes code for providing telemetry for general measurement of vaporizer behavior including but not limited to usage analytics, cartridge and/or battery life, vaporizer heat measurements, and delivery of data to third party health services.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Construction:

An illustrative watch embodiment of a compact wearable inhaler, vaporizer and/or atomizer of the present invention is shown in FIGS. 1-11.

Figure 1:
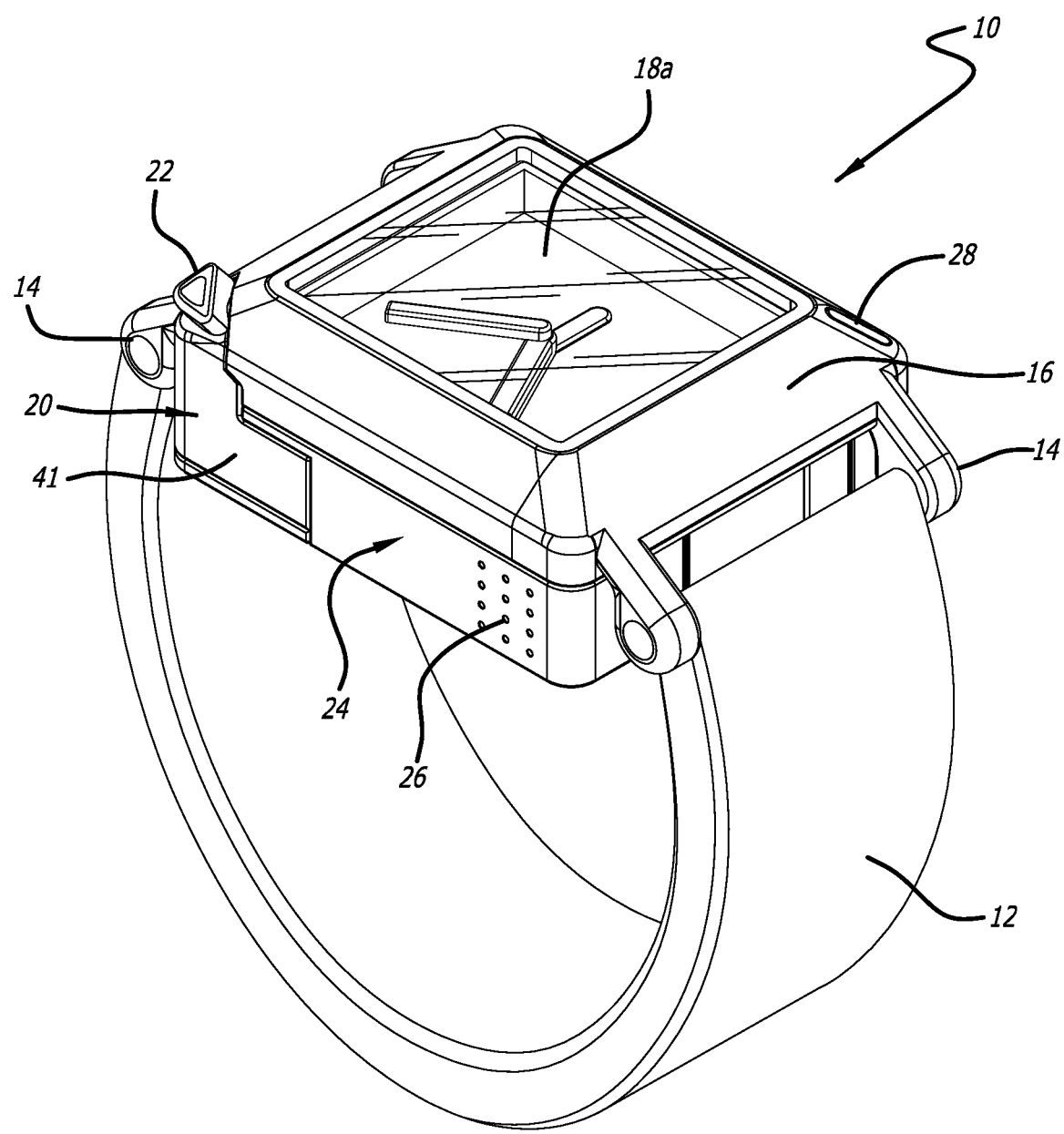
FIG. 1 is a perspective view of a fully assembled vape watch implemented in accordance with an illustrative embodiment of the present teachings.

FIG. 1 is a perspective view of a fully assembled vape watch assembly 10 implemented in accordance with the present teachings. As shown in the figure, the vape watch assembly 10 includes a watch module 18a mounted within a watch housing or frame 16. In the best mode, the housing is metallic or plastic in construction. However, the invention is not limited thereto. That is, other materials may be used without departing from the scope of the present teachings.

The vape watch assembly and housing are dimensioned to fit on a wrist of a user. Accordingly, in the best mode, the approximate external dimensions are 38 to 51 mm in length, 25-44 mm in width and 8 to 16 mm in depth.

The housing 16 allows for interchangeable watches to be integrated: smart, LCD, digital, or analogue. As discussed below, the smart watch assembly 10 is adapted to communicate with a vape circuit and an app via Bluetooth or direct connection with the ability to transmit relevant data to a receiving application. The frame 16 couples to a watch band or wrist band 12 via pins 14.

The assembly 10 includes a vape cartridge 20 secured in a cartridge housing 24. The cartridge 20 may be implemented in accordance with the teachings of U.S. Pat. No. 9,549,573 entitled Vaporization Device Systems and Methods issued Jan. 24, 2017 to James Monsees et al., the teachings of which are hereby incorporated herein by reference, with certain modifications for the present application. The cartridge 20 may be of custom design as disclosed and claimed in copending patent application Ser. No. 15/264,508 or an off-the-shelf unit purchased from companies such as Juul (www.juul.com).

In the illustrative embodiment, the cartridge housing 24 has air intake holes 26. A mouthpiece 22 is located on one corner of the watch housing 16. In the illustrative embodiment, the mouthpiece 22 is made of silicone or other suitable material. An LED lens 28 is provided on the watch housing 16 to convey illumination from an LED 38 (FIG. 3), via aperture 34, when a user puts his or her mouth on mouthpiece 22 and inhales.

Figure 2:
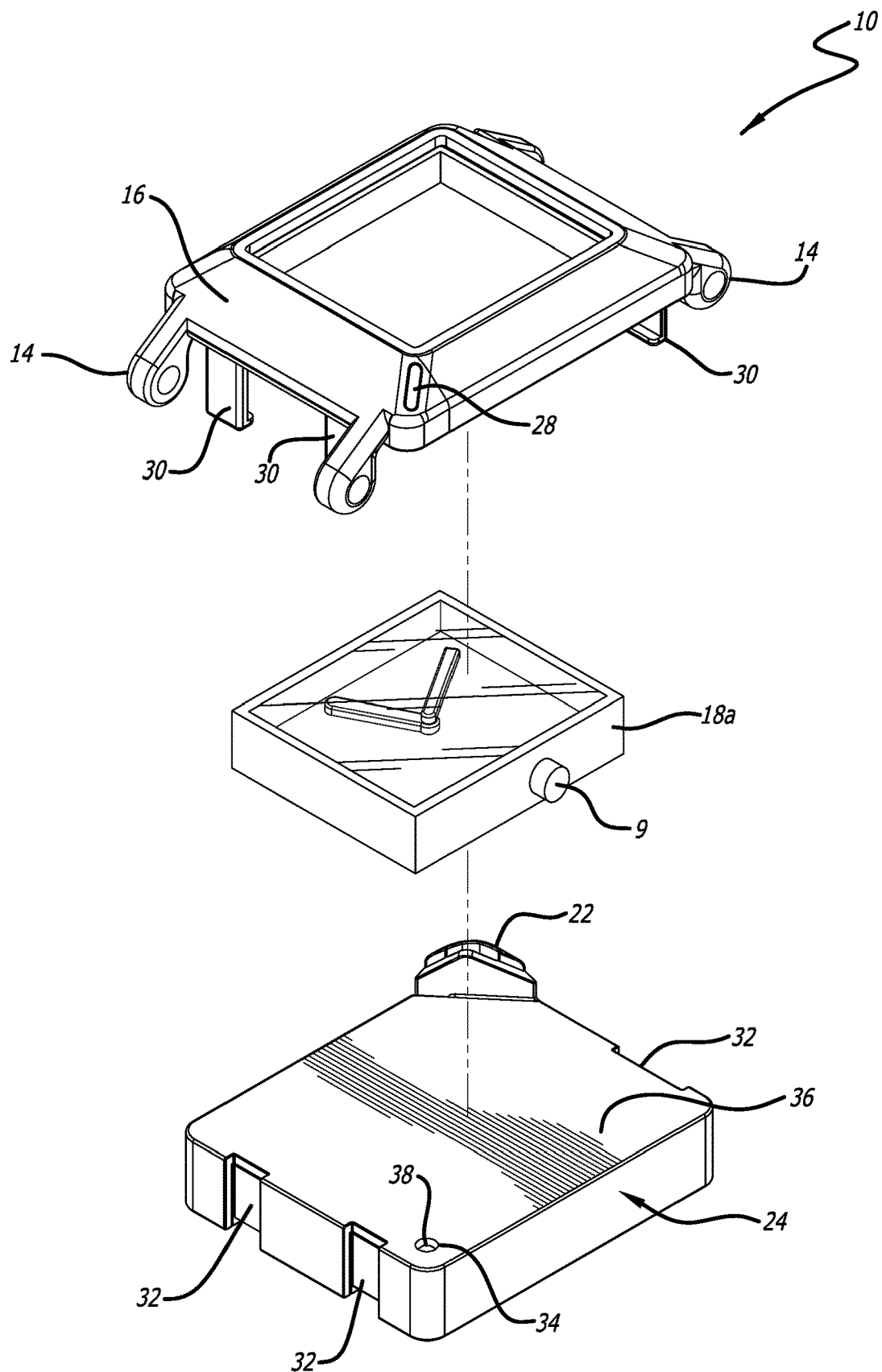
FIG. 2 is an exploded perspective view of the vape watch of FIG. 1 showing a watch housing with snap legs that slide into recesses and snap under the underside of cartridge holder.

FIG. 2 is an exploded perspective view of the vape watch assembly 10 of FIG. 1 with the band 12 thereof removed. FIG. 2 shows snap legs 30 extending from the housing 16. The legs 30 slide through recesses 32 of the cartridge housing 24 and snap under the underside thereof. The legs 30 ensure that the watch module 18a is sandwiched between the top surface of the cartridge housing 24 and the underside of watch housing 16. A stem 9 is provided to set the watch 18a.

Figure 3:
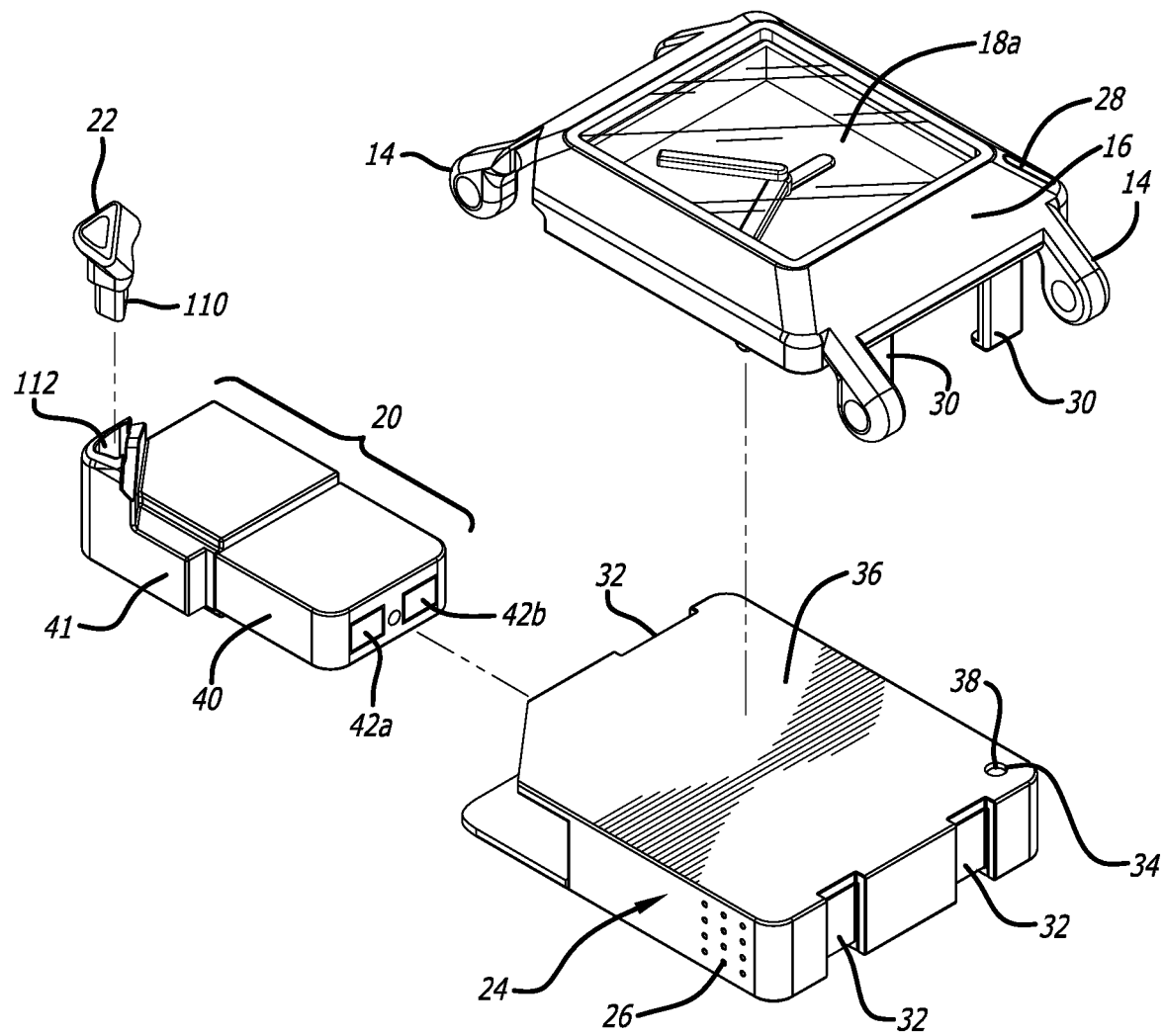
FIG. 3 is a partially disassembled perspective view of the vape watch of FIG. 1 showing the vape cartridge removed from the cartridge housing.

FIG. 3 is a partially disassembled perspective view of the vape watch of FIG. 1 showing the vape cartridge assembly 20 removed from the cartridge housing 24. In FIG. 3, the mouthpiece 22 is removed from cartridge housing 24 to reveal a lower neck 110 that seats in an aperture 112 in the cartridge housing 24. The aperture 112 can be configured to receive mouthpiece 22 of any suitable design and construction.

Figure 3A:
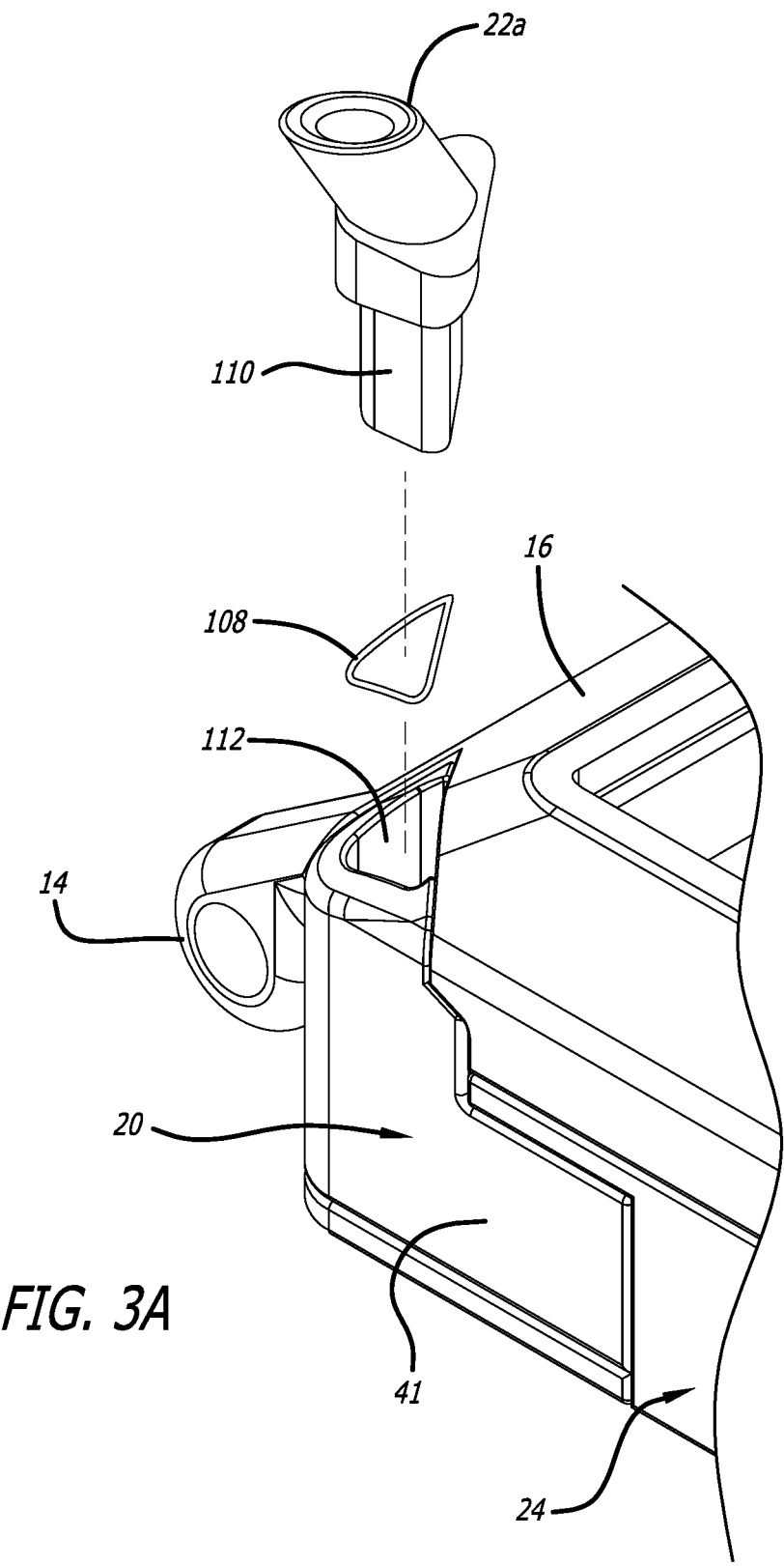
FIG. 3A is a perspective fragmented view of an alternative embodiment of the vape watch of FIG. 1 showing a first alternative mouthpiece adapted for insertion into an aperture thereof with an optional O-ring seal.

FIG. 3A is a perspective fragmented view of an alternative embodiment of the vape watch 10 of FIG. 1 with a first alternate mouthpiece 22a adapted for insertion into aperture 112 thereof with an optional O-ring seal 108. The original mouthpiece has a triangular shape to match the corner of the watch housing 16, however, a cylindrical mouthpiece 22a may be more comfortable for some users. The mouth pieces 22, 22a are removable and replaceable so that multiple people may use the device 10 and each may have their own mouthpiece for sanitary purposes. The mouth pieces include snap in closing mechanisms and may be all metal, all plastic, all rubber or metal with rubber sleeve or rubber O-ring for the bottom of mouth piece.

Figure 3B:
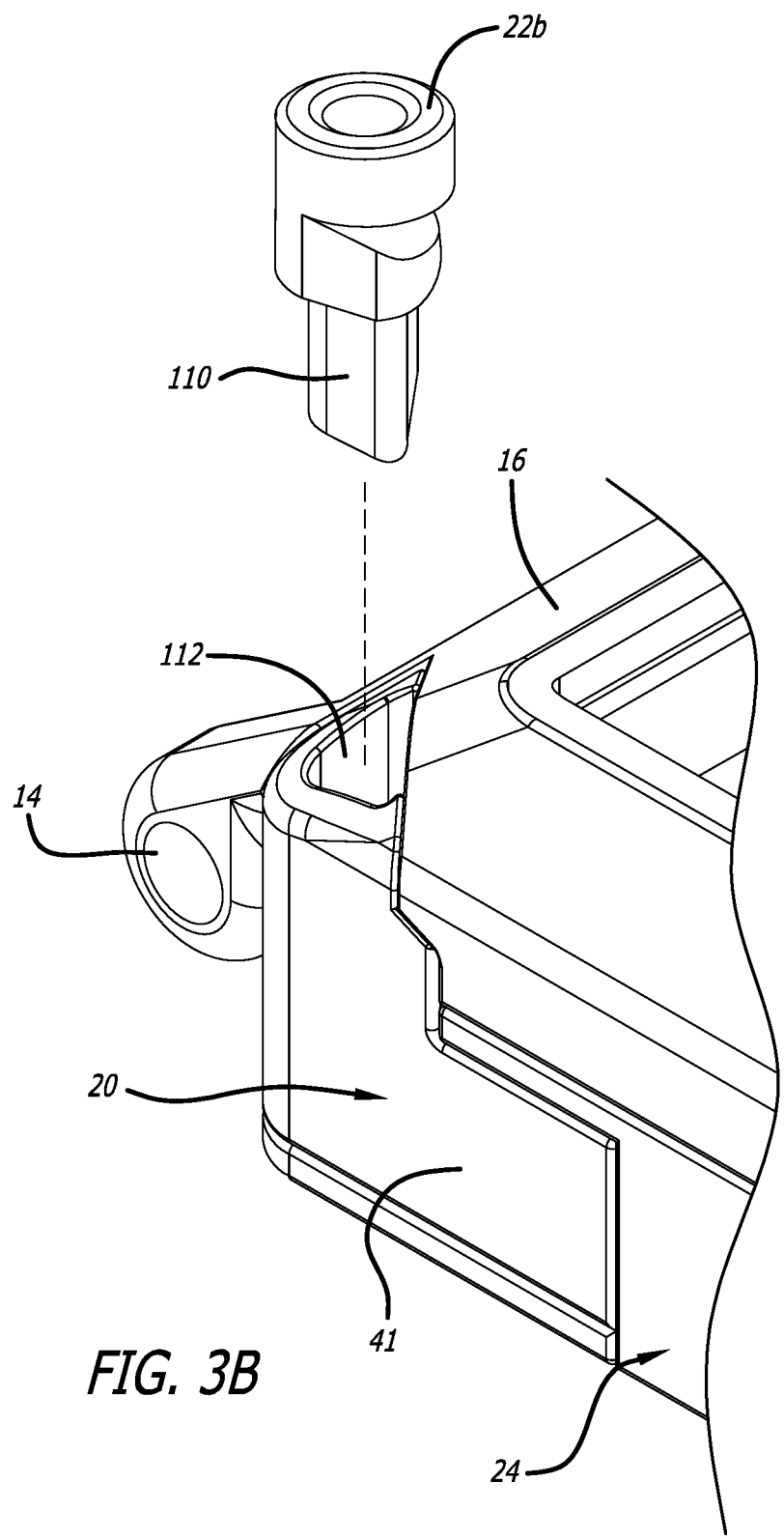
FIG. 3B is a perspective fragmented view of an alternative embodiment of the vape watch of FIG. 1 showing a second alternative mouthpiece adapted for insertion into an aperture thereof.

FIG. 3B is a perspective fragmented view of an alternative embodiment of the vape watch of FIG. 1 showing a second alternate mouthpiece adapted for insertion into an aperture thereof and lock the cartridge 20 into the housing 16.

Figure 4:
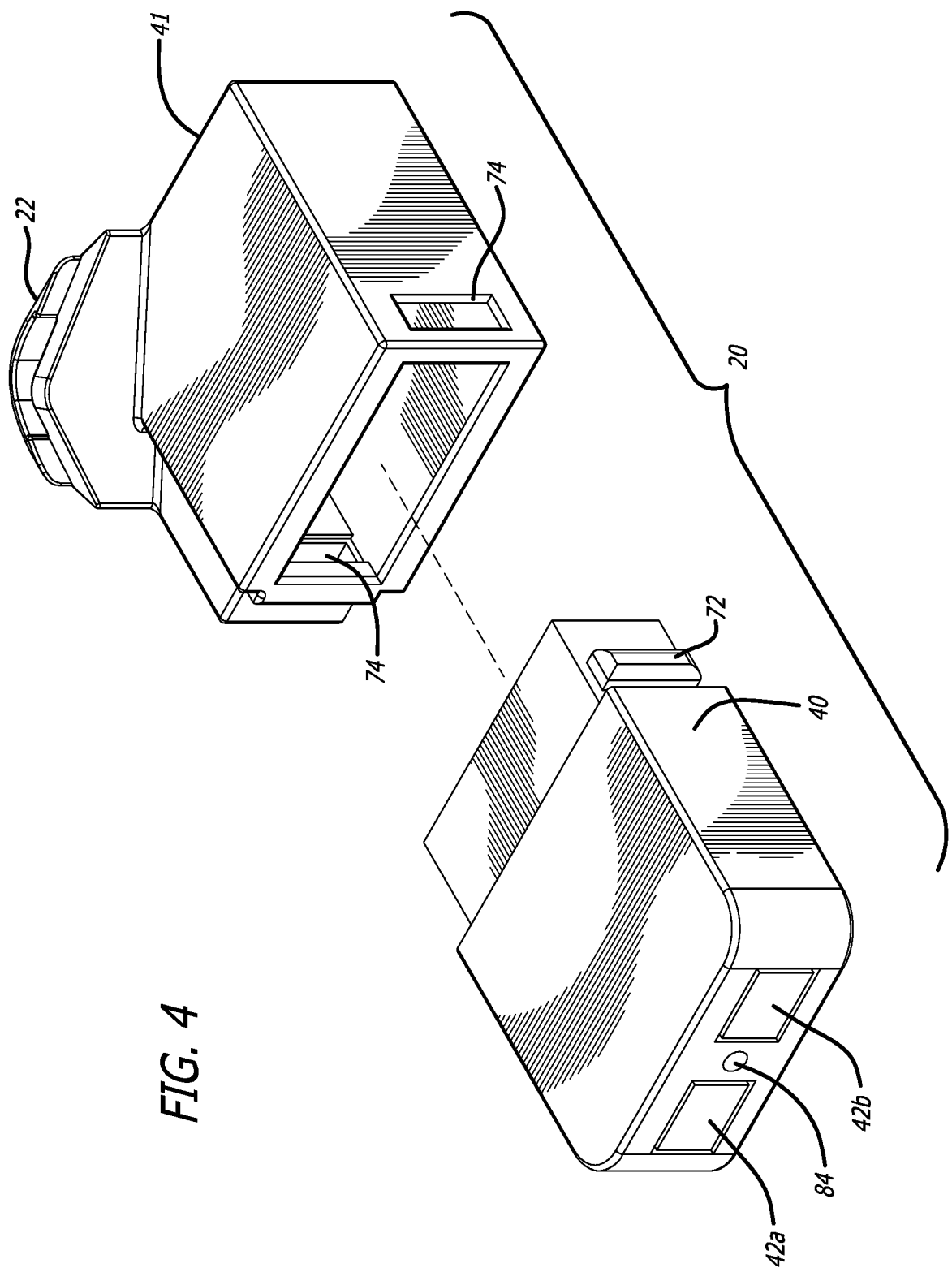
FIG. 4 is a perspective disassembled view of the cartridge assembly of the vape watch of the present invention.

FIG. 4 is a perspective disassembled view of the cartridge assembly 20 of the vape watch 10 of the present invention. As shown in FIG. 4, the vape cartridge assembly 20 has an inner (lower) section 40 and an outer (upper) section 41 that slide together and interlock in the manner shown in FIG. 4. The inner and outer housing sections 40 and 41 respectively engage via relative linear translation and are secured in an airtight engagement thereafter by locking tabs 72 (on the cartridge 40) and detent recesses 74 on outer housing section 41. Electrical contacts 42a and 42b engage contacts 43a and 43b respectively as disclosed more fully below in FIG. 7. An air inlet hole 84 is provided in the inner section 40 to allow for air to enter a vaporizing chamber 81 shown in FIG. 5 and engage an air switch 66 through O-ring 88.

Figure 5:
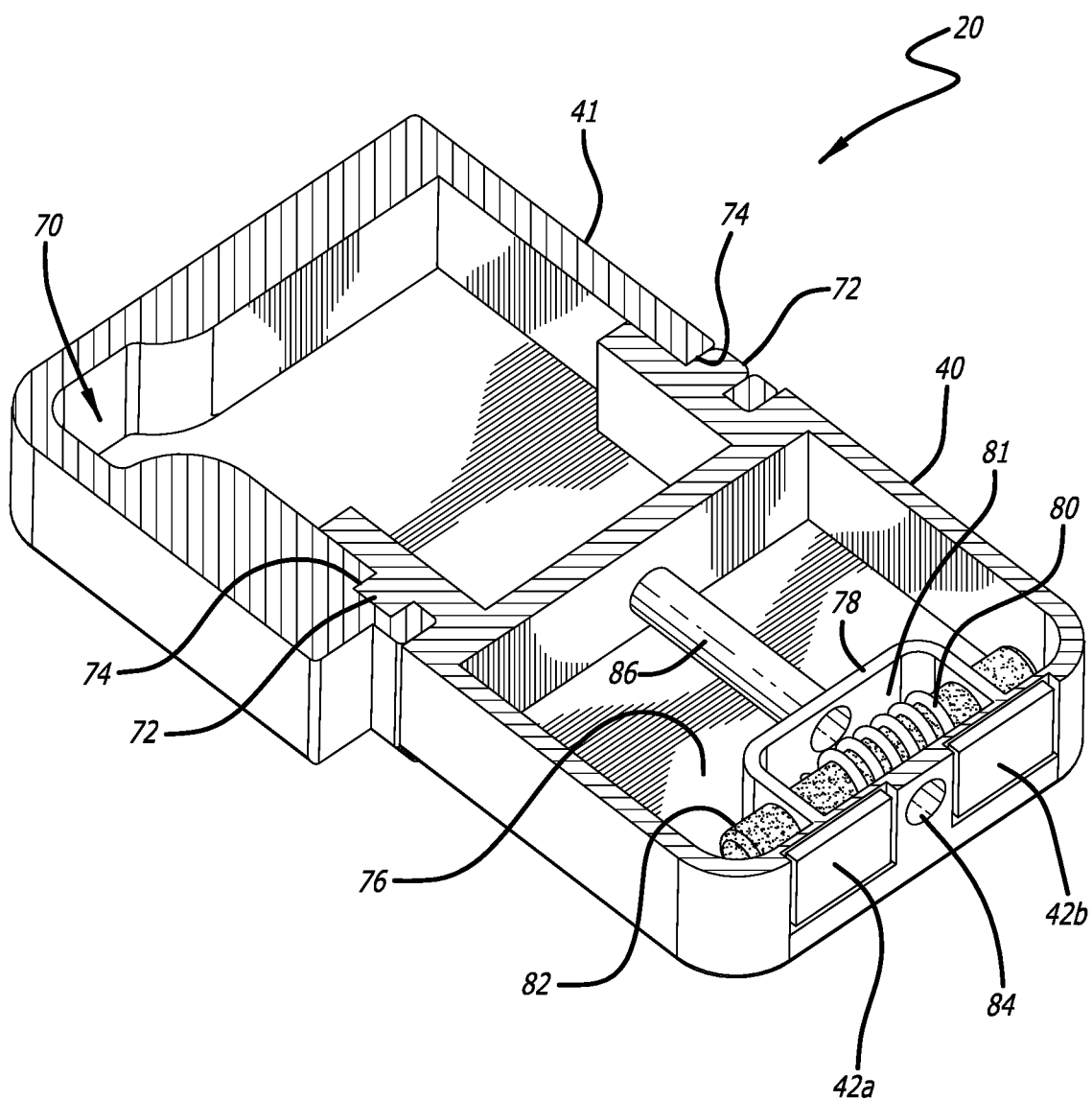
FIG. 5 is a perspective view of the cartridge shown in FIG. 4 with the cover removed to reveal the coil, wick and expansion chamber thereof.

FIG. 5 is a perspective disassembled view of the cartridge assembly 20 with the cover removed to reveal the coil, wick and expansion chamber thereof. As shown in FIG. 3, the cartridge housing 24 includes a receiving aperture 112 for the mouthpiece 22. In FIG. 5, the expansion chamber 70 is shown in fluid communication with the aperture 112. The expansion chamber 70 is in fluid communication with the vaporizing chamber 81 via a pipe 86 held in place by a wall 78 relative to a coil 80 and wick 82. Hence, when suction is applied to the mouthpiece 22 (FIGS. 1-3), air is drawn into the vaporizing chamber 81 via the aperture 84.

Figure 6:
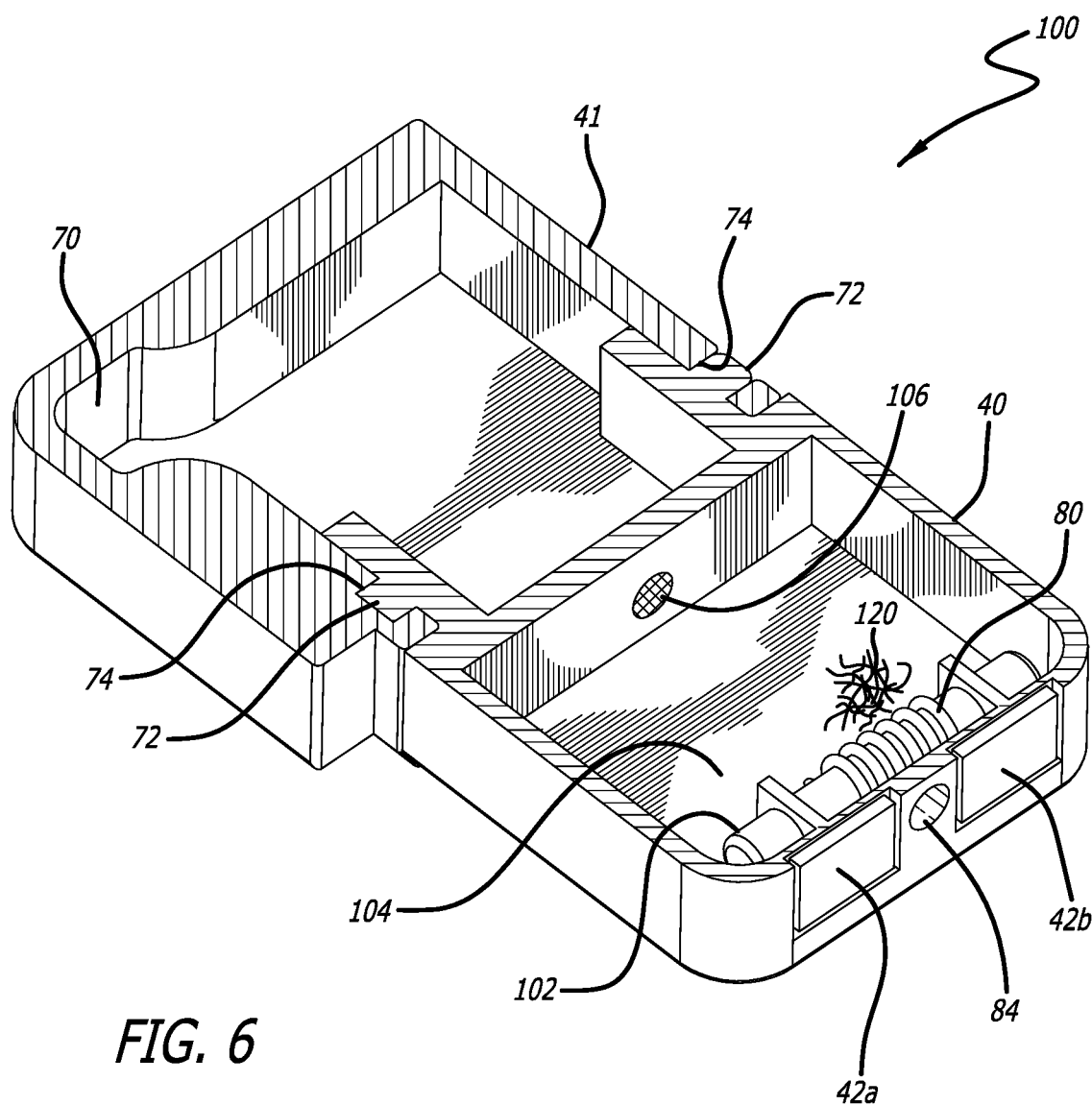
FIG. 6 is a perspective view of the cartridge shown in FIG. 6A with the pipe between the vaporizing chamber and the expansion chamber removed and replaced with a screen.

FIG. 6 is a perspective view of an alternative embodiment of the cartridge shown in FIG. 5 with the pipe between the vaporizing chamber and the expansion chamber removed and replaced with a screen 106. In this embodiment, the wick 82 is replaced with a quartz rod 102 and tobacco 120 is placed in the chamber 104.

Figure 7:
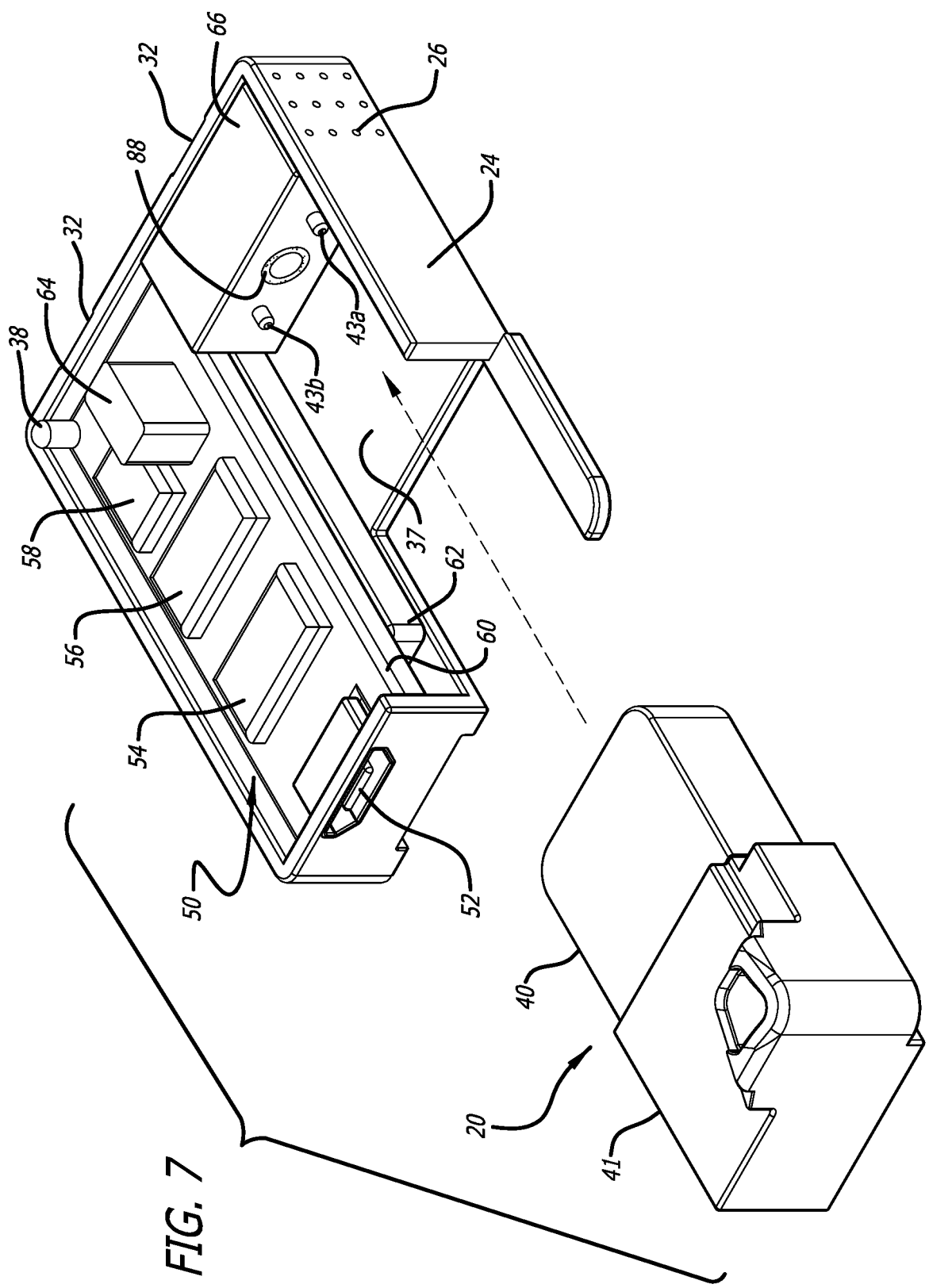
FIG. 7 is a perspective view of the interior chamber of the cartridge housing of the vape watch of FIG. 1 with the top removed to show PC board assembly air switch and electric pin connectors.

FIG. 7 is a perspective view of the interior chamber of the cartridge housing 24 of the vape watch assembly 10 of FIG. 1 with the top removed to show PC board assembly 50. As shown in FIG. 7, the vape cartridge assembly 20 slides into a channel 37 and is retained by the vaper cartridge housing 24.

The PC board assembly 50 includes a micro USB socket 52, microprocessor 54 for regulating charging and vape activation, memory 56 and WIFI/Bluetooth transceiver 58 mounted all on a PC board 60. A rechargeable battery 62 is stored under PC board 60 and recharged through the USB port 52.

First and second electrical contacts 43a and 43b are electrically coupled to the bus (not shown) of the PC board and engage mating contacts 42a and 42b on the vape cartridge assembly 20 shown in FIGS. 3-6. Contacts 42a and 42b are connected to the internal heating coil and facilitate electrical connection and control via the microprocessor 54 as discussed more fully below.

Figure 8:
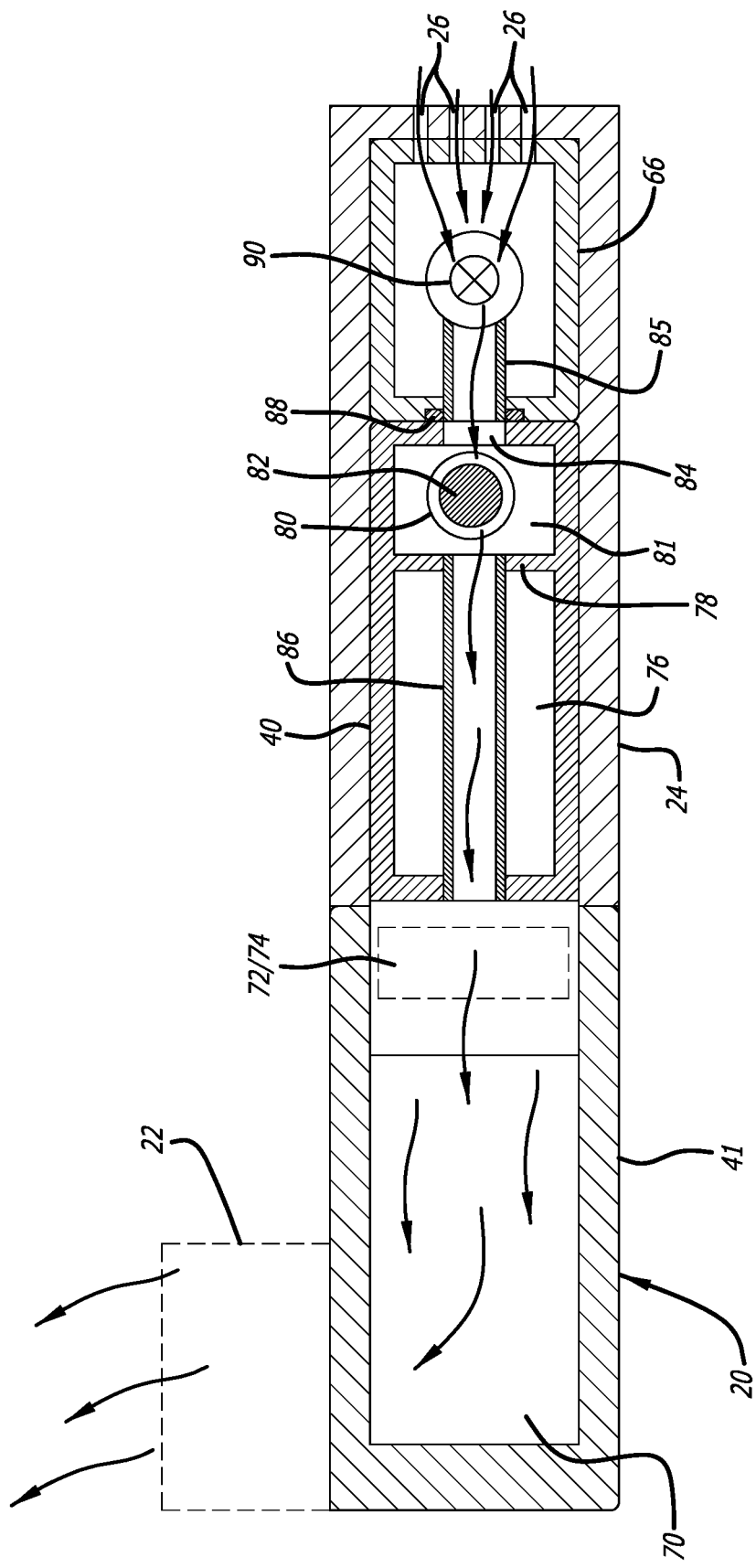
FIG. 8 is a sectional side view of the vape cartridge of FIG. 5.

FIG. 8 is a sectional side view of the vape cartridge of FIG. 5. As shown in FIG. 8, an air flow sensor 90 is mounted within an air inlet chamber 66 in fluid communication with aperture 84 (FIG. 5) via a pipe 85 surrounded by an O-ring seal 88. Air drawn in through vent holes 26 move vapors coming off wick 78 in response to heat from coil 80 to expansion chamber 70 via pipe 86. The vapor is collected in the expansion chamber 70 before inhalation by the user via the mouthpiece 22.

The air sensor also activates a hit counter and timer provided by the microprocessor 54 which regulates numerous functions relating to the dosage of vapor applied to user including the duration and intensity of the activation of the coil and volume of the vapor released. In addition, the microprocessor keeps track of the amount of fluid stored in chamber 76 and how much is left in the cartridge and displays this and other relevant information to the user such as measurements of amount consumed, battery life, how many hits were taken and frequency of consumption many metrics via the display in the smartwatch embodiment disclosed herein.

Methods of inserting oil into the cartridge 20 and for attaching an end piece that includes a heating coil and air flow sensor are currently known and in the public domain.

The LED 38 is activated by an air flow sensor switch 90, as will be explained below, so the user can have a visual confirmation that the device 10 is working properly.

Figure 9:
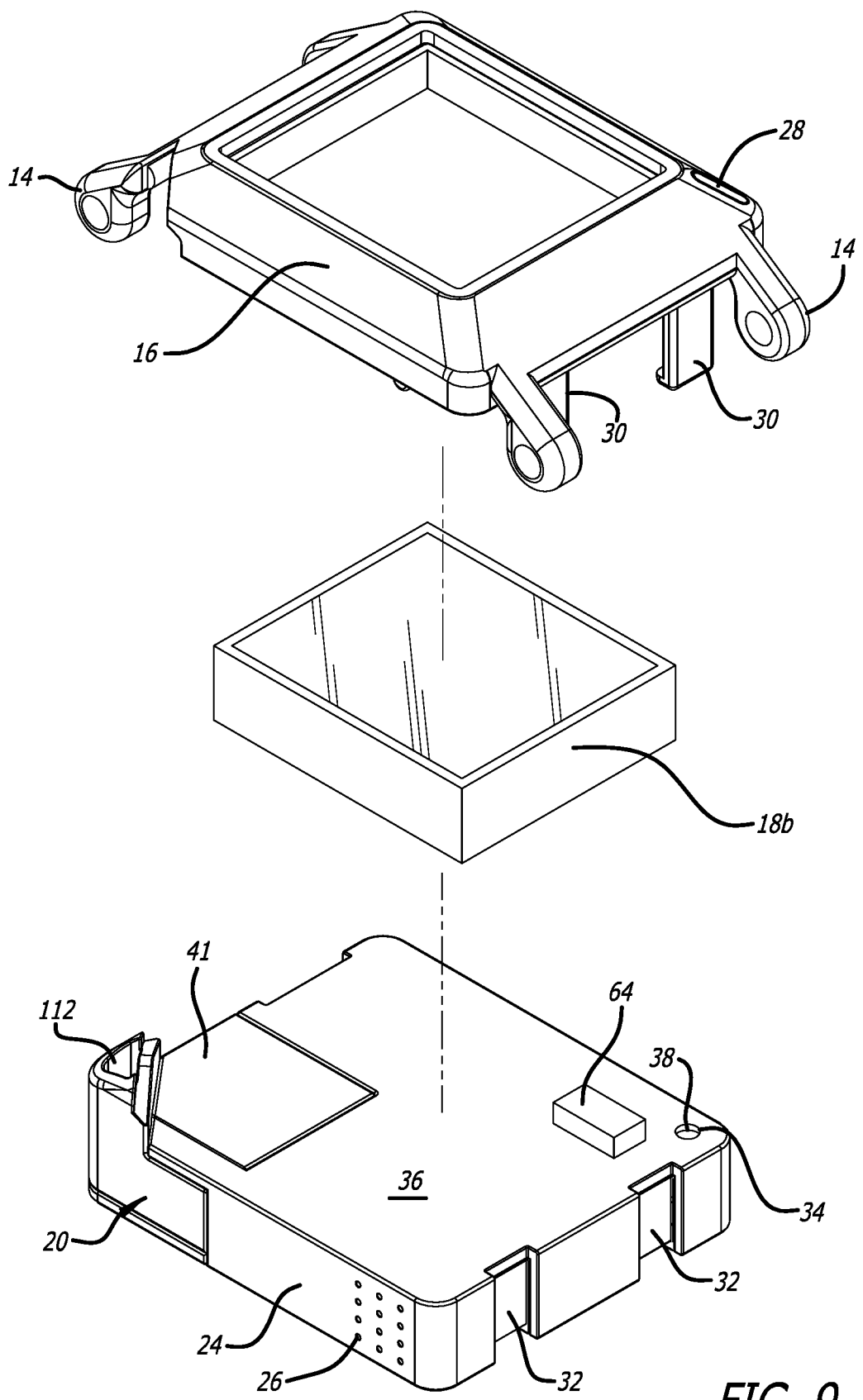
FIG. 9 is an exploded view of the vape watch of FIG. 1 showing an alternative digital watch embodiment.

FIG. 9 is an exploded view of the vape watch of FIG. 1 showing an alternative digital watch embodiment 18*b*. An electrical connector 64 is attached to the PC board 60. As shown in FIG. 9, the connector 64 protrudes through the top cover 36 of cartridge holder 24 and connect mating contacts under the base of a smart watch module 18*b*. This allows the watch 18*b* to be able to be controlled by a phone app adapted to program a watch face display.

Figure 9A:
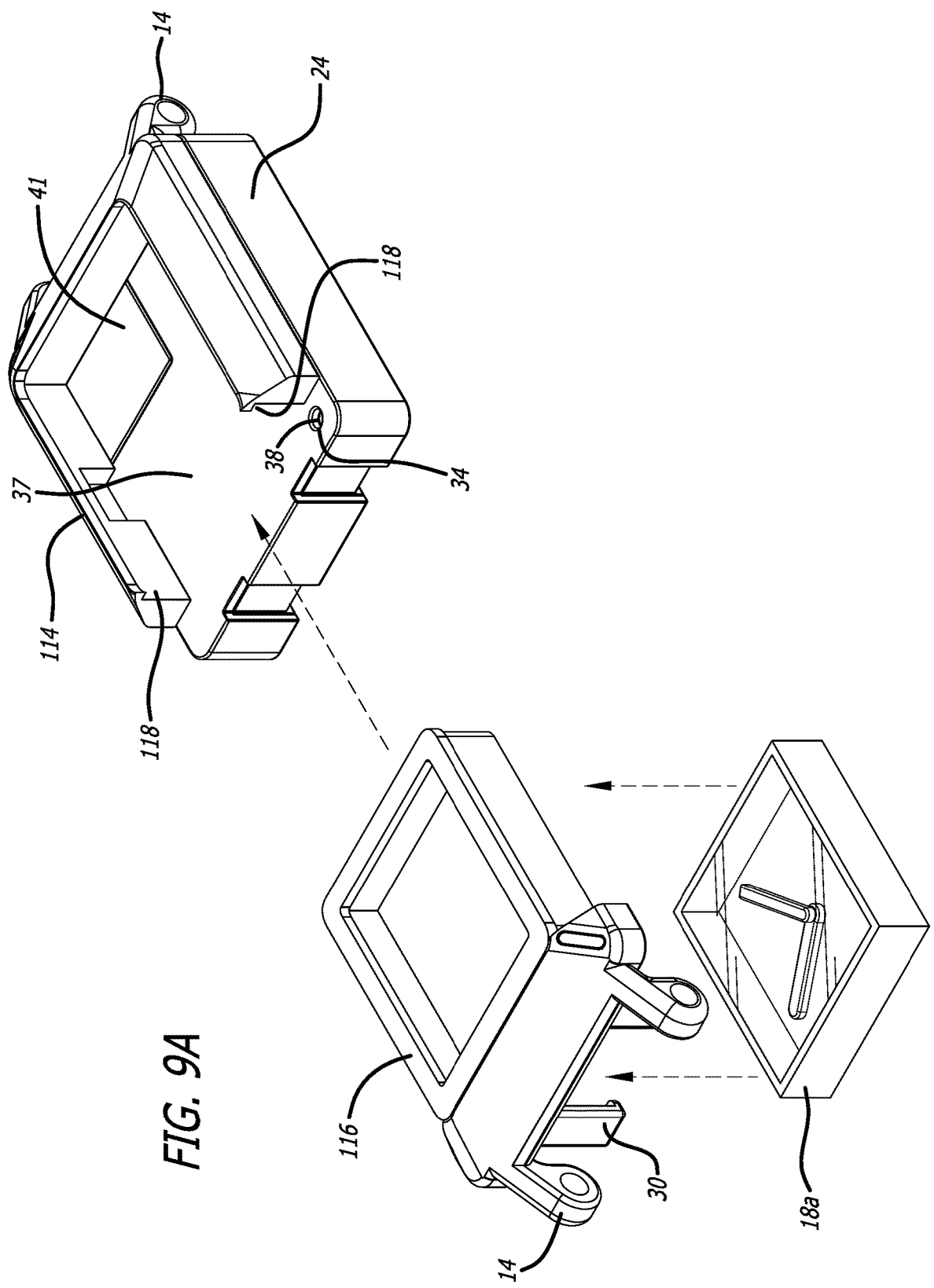
FIGS. 9A and 9B are exploded views of an alternative embodiment of the vape watch of FIG. 1 designed to accommodate a watch module that is inserted vertically into the housing and then horizontally into the housing respectively.
Figure 9B:
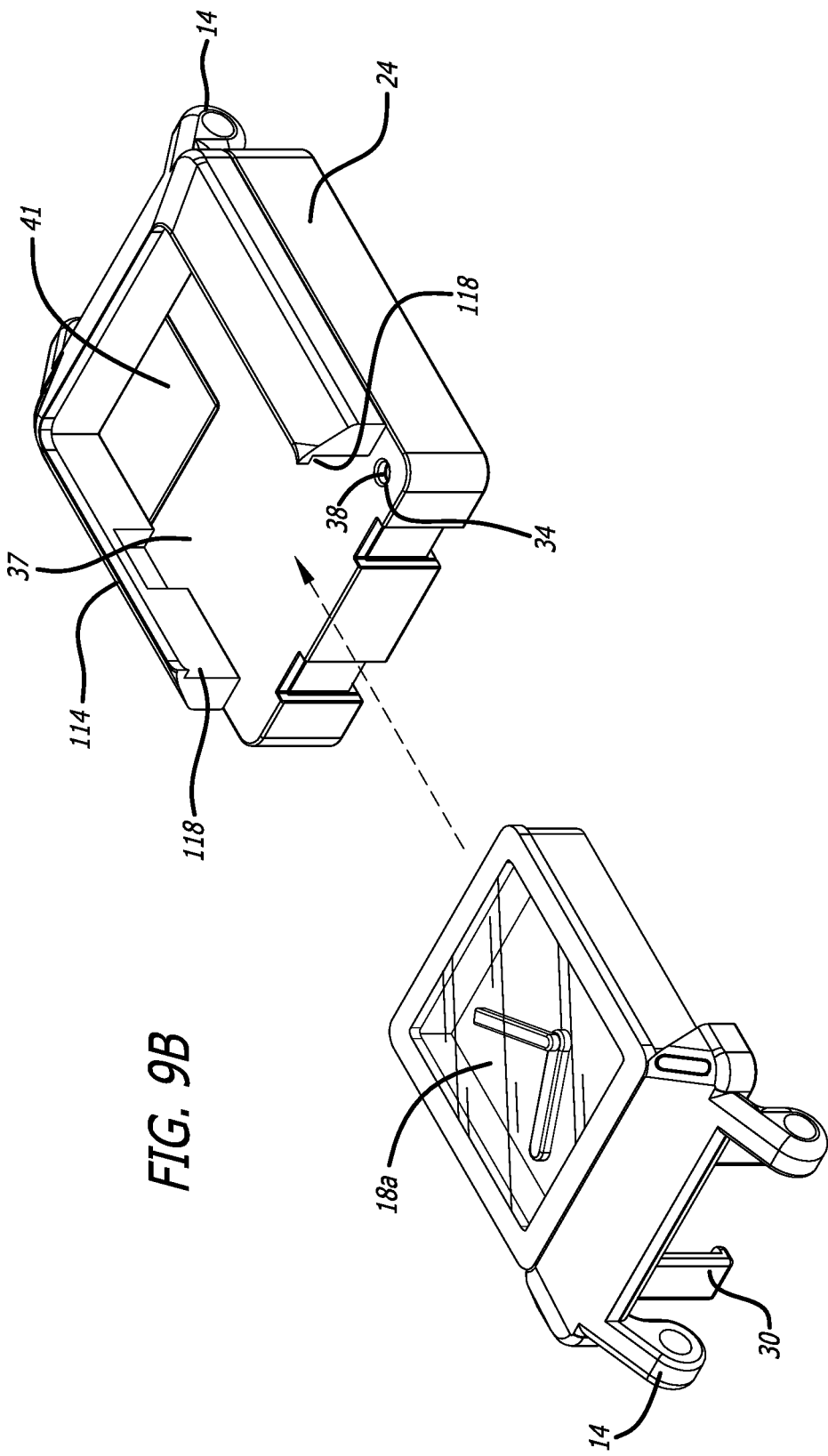

FIGS. 9A and 9B are exploded views of an alternative embodiment of the vape watch of FIG. 1 designed to accommodate a watch module that is inserted vertically into the housing and then horizontally into the housing. That is, as shown in FIG. 9A, the vape watch is inserted vertically into the housing 116 and together, these elements are linearly translated (orthogonal or horizontal relative to the motion of the module 18*a* into the housing 116) into channel 37 of the outer border of the modified slide in adapter 114 as shown in FIG. 9B.

Figure 10:
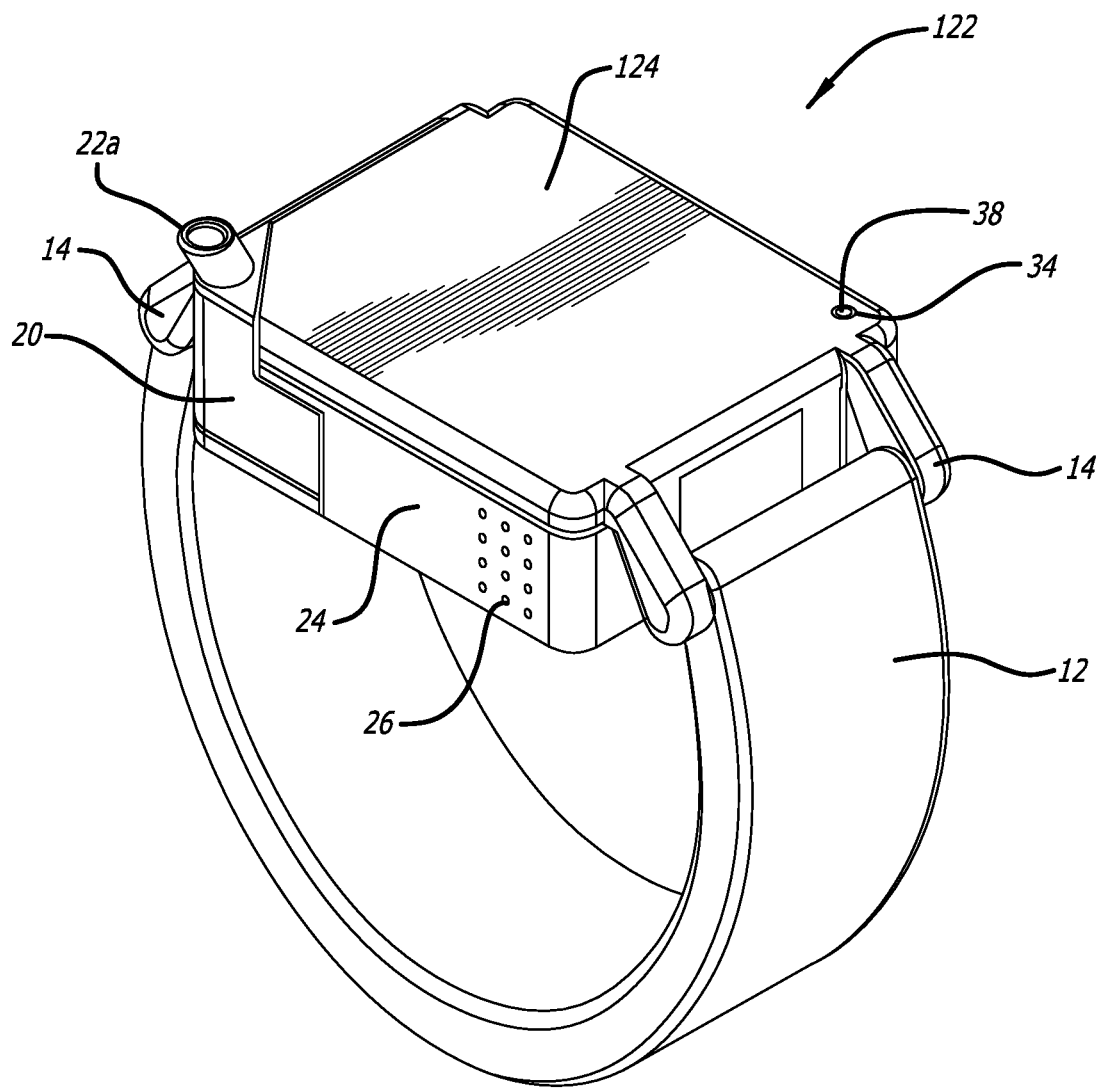
FIGS. 10 and 11 are perspective and elevated views respectively showing an alternative embodiment of the invention without a watch to provide a wrist wearable vaporizer device in accordance with the present teachings.
Figure 11:
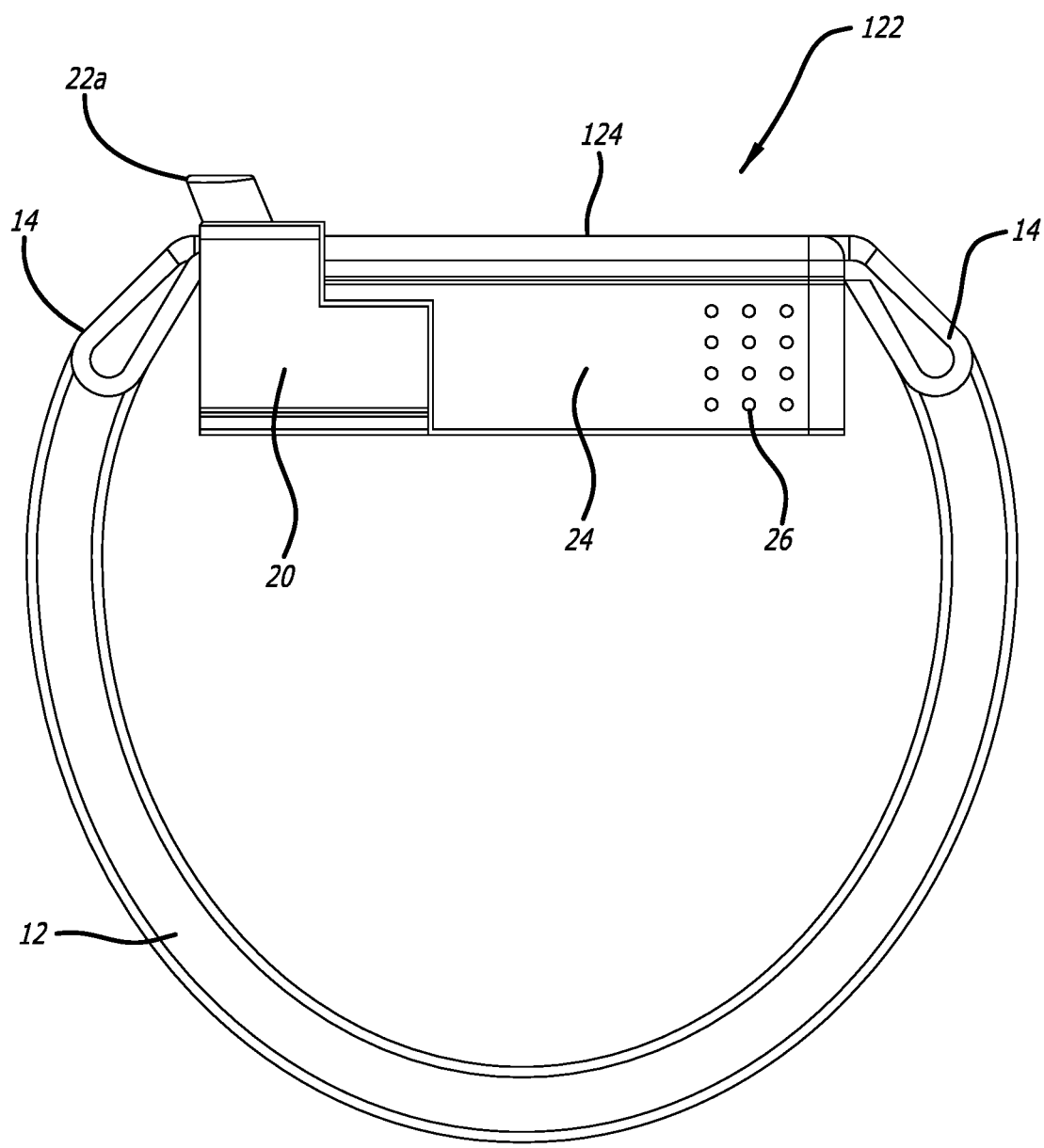

FIGS. 10 and 11 are perspective and elevated views respectively showing an alternative embodiment of the invention without a watch to provide a wrist wearable vaporizer device in accordance with the present teachings.

Operation:

Initially, firmware is stored in memory 56 for execution by processor 54 to provide operational control for the device 10 and enable user input and output via the transceiver 58 with respect to user preferences. The cartridge 20 loaded with fluid is inserted and the device 10 is then assembled as discussed above. After assembly, the user can draw on a mouthpiece 22, 22*a*, or 22*b* to inhale vapor, smoke, or medication.

The user will have visibility of a display light that shines through the corner of the device when in use. The user will be able to remove and change the battery, PC board, the wireless transceiver, cartridge, electrical connector, mouth piece, bezel, various types of watches, and screens from the device. The watch or screen can slide on and off or be locked into place via a bezel/lock hybrid.

In the illustrative embodiment, the device is coupled to a wristband enabling it to be worn as a watch. However, the device may also be removed and worn as armband, anklet, bracelet, belt or necklace or carried in a pocket, purse or pouch. The mounting arrangement(s), e.g. wristband, bracelet, belts, etc., can provide additional battery and inhalant storage compartments. Thus, the present teachings are not limited to a watch implementation. The compact, novel, modular design could also be implemented in other objects or devices without departing from the scope of the present teachings.

The device may be used to vaporize solid as well as liquid organic and inorganic herbs, chemicals, compounds and medicines. A breath freshener may be used in place of the inhalant. The device may be used as a pipe to burn tobacco and/or other plants. The smartwatch may be replaced with a simple plastic or glass lid and it may be tinted or transparent. The device may be worn upside down and used to read a user's pulse. With the smartwatch, the device could be used as a thermometer and could be solar powered via a solar cell mounted on the lid or on the wristband or watchband. A heating coil (not shown) is located within cartridge 20 which holds oil or other compounds such as nicotine or flavoring liquids.

As is well known in the art, the smartwatch is an electronic circuit with a processor, a memory fixed in a tangible medium, a wireless transceiver and a touchscreen display. Software for implementing a variety of functions is provided in either the smartwatch, or the associated smart phone or other computer to which it is coupled via a wireless connection. Those functions include by way of example tracking and displaying the status of the device, scheduling medication use, monitoring and displaying the level of inhalant remaining via a sensor and LED (not shown) mounted in the housing and electrically coupled to the smartwatch or an integrated rear camera, activation of the heating element and/or displaying the status of same, sending a notification to a friend or family member that the emergency dose of inhalant has been used, etc. The software provides data to an associated health application on a user's smart phone. When the heating element is activated, the display on the device is programmed to change to show a flame or other symbol or image to indicate that the heating element is activated.

In short, an application is included that is adapted to run on a smartphone to allow a user to control the watch via the microprocessor 54 and the wireless transceiver 58. In addition, the app allows the user to select, gather, use, and apply numerous metrics (alarms, tracking, limitation setting, etc.) of the individual user's consumption of the dispensed fluid, oil, medication, or particle. The app will also allow the user to receive notifications of the level of liquid in the cartridge 20 and the number of inhalations remaining before replacement is needed.

Those having ordinary skill in the art and access to the present teachings will recognize additional modifications, applications and embodiments within the scope thereof. For example, the invention is not limited to the size, shape, number or location of the input or output ports used in connection with the device.

It is therefore intended by the appended claims to cover any and all such applications, modifications and embodiments within the scope of the present invention.

The invention claimed is:

1. A compact wearable modular multifunctional inhalation device comprising:
    a housing;
    a removable cartridge module adapted to seat within the housing, the cartridge module including:
        a chamber mounted within the cartridge module for storing a source of inhalant,
        an aperture operationally coupled to the chamber and adapted to be accessible externally when the inhalation device is fully assembled and a heating element mounted within the cartridge module for heating the source of inhalant;

a removable modular electronic circuit adapted to seat within the housing to provide electrical current to the heating element; and a mechanism coupled to the housing for wearing the device, whereby, when the device is assembled, inhalation is adapted to be drawn from the chamber in the cartridge module through the aperture by inhalation while the inhalation device is worn by a user.

2. The device of claim 1 further including a removable modular electronic display adapted to seat within the housing.

3. The device of claim 1 wherein the electronic circuit includes a processor and memory.

4. The device of claim 3 wherein the memory includes software for execution by the processor.

5. The device of claim 4 wherein the software includes code for activating the heating element and displaying the status of the heating element.

6. The device of claim 5 wherein the software includes code for monitoring the status of the source of inhalant and/or a source of electrical potential.

7. The device of claim 3 further including a transceiver.

8. The device of claim 7 further including an application adapted to run on a mobile communications and computing platform for communicating with said inhalation device via said transceiver and said processor.

9. The device of claim 1 further including a switch for activating the heating element.

10. The device of claim 9 wherein the switch is activated by air flow.

11. The device of claim 1 wherein the mechanism for wearing the device is a wristband.

12. The device of claim 1 wherein the source of inhalant includes a fluid.

13. The device of claim 12 wherein the device includes a wick having a distal end and a proximal end, the distal end being in fluid communication with fluid in the chamber.

14. The device of claim 1 further including a mouthpiece adapted to be mounted in the aperture in the cartridge module.

15. The device of claim 14 wherein the mouthpiece is located on one corner of the housing when the cartridge module is seated within the housing.

16. The device of claim 14 wherein the mouthpiece is removable.

17. The device of claim 14 wherein the mouthpiece is replaceable.

* * * * *